United States Patent [19]

Matsuo et al.

[11] Patent Number: 4,921,887

[45] Date of Patent: May 1, 1990

[54] THIAZOLE COMPOUNDS AND PHARMACEUTICAL COMPOSITION COMPRISING THE SAME

[75] Inventors: Masaaki Matsuo, Toyonaka; Takashi Manabe, Osaka; Shinji Shigenaga, Kobe; Hiroshi Matsuda, Osaka, all of Japan

[73] Assignee: Fujisawa Pharmaceutical Company, Ltd., Osaka, Japan

[21] Appl. No.: 270,628

[22] Filed: Nov. 14, 1988

[30] Foreign Application Priority Data

Nov. 16, 1987 [GB] United Kingdom ............... 8726763

[51] Int. Cl.⁵ ................. A61K 31/445; A61K 31/455
[52] U.S. Cl. ..................................... 514/326; 514/318;
546/209; 546/193; 546/194
[58] Field of Search .............. 546/209, 193, 194; 514/326, 318

[56] References Cited

U.S. PATENT DOCUMENTS 2,636,037  4/1953  Sprague et al. .................. 546/209
4,742,057  5/1988  Ueda et al. ....................... 546/201

FOREIGN PATENT DOCUMENTS 157420  10/1985  European Pat. Off. ............ 544/386
2536399  5/1984  France ............................. 546/209

OTHER PUBLICATIONS

Search Report for European Patent Application 88118882.5.

Primary Examiner—Robert T. Bond
Attorney, Agent, or Firm—Oblon, Spivak, McClelland, Maier & Neustadt

[57] ABSTRACT

A thiazole compound of the formula:

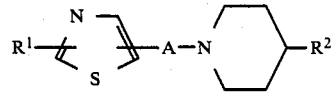

wherein
  $R^1$ is amino or acylamino,
  $R^2$ is ar(lower)alkoxy, and
  A is lower alkylene, and a pharmaceutically acceptable salt thereof, processes for the preparation thereof and pharmaceutical composition comprising the same.

11 Claims, No Drawings

THIAZOLE COMPOUNDS AND PHARMACEUTICAL COMPOSITION COMPRISING THE SAME

This invention relates to new thiazole compounds and pharmaceutically acceptable salts thereof.

More particularly, it relates to new thiazole compounds and pharmaceutically acceptable salts thereof which have antiallergic activity and/or 5-lipoxygenase inhibitory activity, to processes for the preparation thereof, to a pharmaceutical composition comprising the same and to a method for the treatment of allergic disease in human beings or animals.

One object of this invention is to provide new thiazole compounds and pharmaceutically acceptable salts thereof which possess antiallergic activity and/or 5-lipoxygenase inhibitory activity.

Another object of this invention is to provide processes for the preparation of said thiazole compounds or salts thereof.

A further object of this invention is to provide a pharmaceutical composition comprising, as an active ingredient, said thiazole compounds or pharmaceutically acceptable salts thereof.

Still further object of this invention is to provide a therapeutical method for the treatment of allergic disease such as allergic asthma, allergic rhinitis, allergic conjunctivitis, chronic urticaria, or the like, in human beings or animals.

Some thiazole compounds having antiallergic activity have been known as described in European Patent Application Publication No. 224919.

Some piperidino compounds having antiallergic activity have been known as described in European Patent Application Publication No. 157420.

The object thiazole compounds of this invention are new and can be represented by the following general formula [I]:

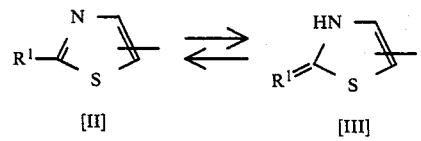

wherein
$R^1$ is amino or acylamino,
$R^2$ is ar(lower)alkoxy, and
A is lower alkylene.

In case that the aminothiazole moiety of the object compound [I] is 2-amino- or 2-acylamino-thiazole, it may also exist as 2-imino- or 2-acylimino-thiazoline, which is a tautomer of aminothiazole as follows:

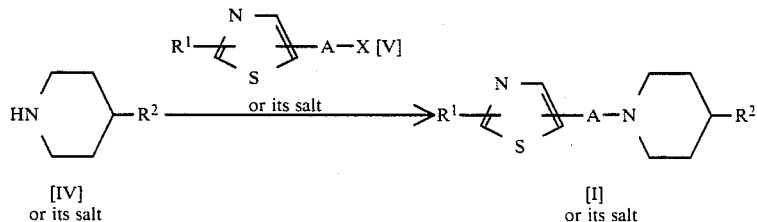

wherein
$R^1$ is amino or acylamino, and
$R^{1'}$ is imino or acylimino.

Both of the above tautomeric isomers are included within the scope of the present invention, and in the present specification and claims, however, they are represented as 2-amino- or 2-acylamino-thiazole for the sake of convenience.

The object compound [I] or its salt can be prepared by processes as illustrated in the following reaction schemes.

Process 1·

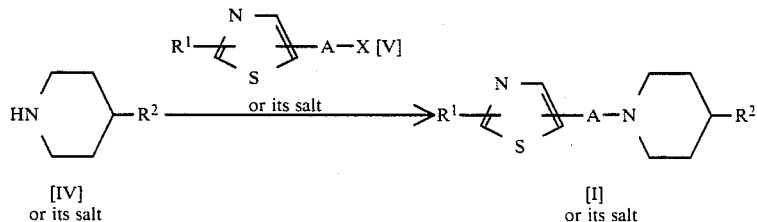

Process 2

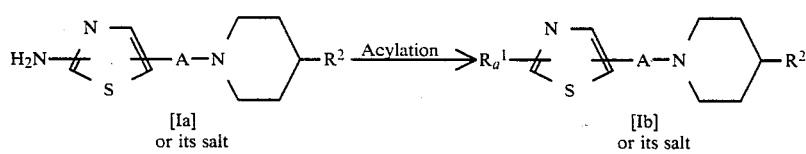

Process 3

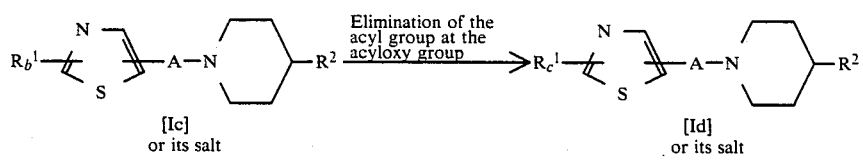

wherein
$R_a^1$ is acylamino,
$R_b^1$ is acylamino substituted with acyloxy,
$R_c^1$ is acylamino substituted with hydroxy,
X is a leaving group, and
$R^1$, $R^2$ and A are each as defined above.

In the above and subsequent descriptions of the present specification, suitable examples of the various definitions to be included within the scope of the invention are explained in detail in the following.

The term "lower" is intended to mean a group having 1 to 6 carbon atom(s), unless otherwise provided.

Suitable "acyl" and acyl moiety in the terms "acylamino" and "acyloxy" may be straight or branched lower alkanoyl [e.g. formyl, acetyl, propionyl, butyryl, isobutyryl, valeryl, isovaleryl, pivaloyl, hexanoxyl, 3,3-dimethylbutyryl, etc.], straight or branched lower alkenoyl [e.g. acryloxyl, crotonoyl, isocrotonoyl, 3-butenoyl, methacryloxy, etc.], mono- or di- or trihalo(lower)alkanoyl [e.g. chloroacetyl, trifluoroacetyl, etc.], cyclo(lower)alkylcarbonyl [e.g. cyclopropylcarbonyl, cyclobutylcarbonyl, cyclopentylcarbonyl, cyclohexylcarbonyl, etc.], lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], hydroxy(lower)alkanoyl [e.g. glycoloyl, lactoyl, 3-hydroxypropionyl, 2-hydroxy-2-methylpropionyl, glyceroyl, etc.], lower alkanoyloxy(lower)alkanoyl [e.g. acetoxyacetyl, acetoxypropionyl, 2-acetoxy-2-methylpropionyl, propionyloxyacetyl, etc.], carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, etc.], aroyl [e.g. benzoyl, toluoyl, xyloyl, naphthoyl, etc.], heterocycliccarbonyl [e.g. furoyl, thenoyl, nicotinoyl, isonicotinoyl, etc.], aralkanoyl [e.g. phenylacetyl, tolylacetyl, naphthylacetyl, 2-phenylpropionyl, 3-phenylpropionyl, 4-phenylbutyryl, tritylcarbonyl, etc.], lower alkylsulfonyl [e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], or the like.

Suitable "ar(lower)alkoxy" may be benzyloxy, phenethyloxy, diphenylmethoxy, diphenylethoxy, diphenylpropoxy, trityloxy, or the like in which the most preferable one is diphenylmethoxy.

Suitable "lower alkylene" may be a straight or branched one such as methylene, ethylene, trimethylene, methylethylene, tetramethylene, ethylethylene, pentamethylene, hexamethylene or the like.

Suitable "leaving group" may be an acid residue such as halogen [e.g. chlorine, bromine, fluorine and iodine], sulfonyloxy [e.g. mesyloxy, tosyloxy, phenylsulfonyloxy, etc.], or the like.

Suitable pharmaceutically acceptable salts of the object compound [I] are conventional non-toxic salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobomide, sulfate, phosphate, etc.], a salt with an amino acid [e.g. aspartic acid, salt, glutamic acid salt, etc.], and the like With respect to the salts of the compounds [Ia] to [Id] in the Processes 2 and 3, it is to be noted that these compounds are included within the scope of the compound [I], and accordingly the suitable examples of the salts of these compounds are to be referred to those as exemplified for the object compound [I].

The processes for preparing the object compounds [I] of the present invention are explained in detail in the following.

Process 1

The object compound [I] or its salt can be prepared by reacting a compound [IV] or its salt with a compound [V] or its salt.

As suitable examples of the salts of the compounds [IV] and [V], there may be mentioned the same kinds of salt as given for the compound [I].

This reaction is usually carried out in a conventional solvent such as water, an alcohol [e.g. methanol, ethanol, isopropyl alcohol, etc.], dioxane, tetrahydrofuran, N,N-dimethylformamide, methylene chloride, chloroform, tetrachloromethane, or any other conventional solvent which does not adversely affect this reaction, or a mixture thereof.

The reaction is carried out at ambient temperature, under warming or under heating, although the reaction temperature is not critical.

This reaction can also be conducted in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, N-methylmorpholine, pyridine or N,N-dimethylaniline.

This reaction can also be performed in the presence of an alkali metal halide such as sodium iodide or potassium iodide Process 2

The object compound [Ib] or its salt can be prepared by reacting a compound [Ia] or its salt with an acylating agent.

Suitable acylating agents are the corresponding carboxylic acid or sulfonic acid compounds, which are represented by the formula: $R^3$-OH wherein $R^3$ is acyl, and reactive derivatives thereof, and the corresponding isocyanate compounds.

As suitable said reactive derivatives, there may be mentioned acid halides, acid anhydrides, active amides and active esters Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as cyanomethyl ester, methoxymethyl ester, p-nitrophenyl ester, 2,4-dinitrophenyl ester, pentachlorophenyl ester, phenylazophenyl ester, carboxymethylthio ester and N-hydroxysuccinimide ester. The kind of such reactive derivatives can be selected depending on the kind of acyl group to be introduced.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, N-methylmorpholine, pyridine or N,N-dimethylaniline.

In certain reaction condition, the 2-acylimino-3-acyl-thiazoline compound of the formula:

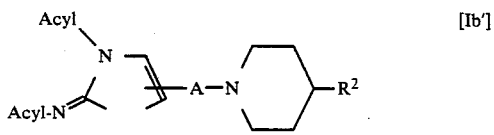 [Ib']

wherein Acyl is acyl, and
$A^2$ and A are each as defined above, may be obtained as by-product. In such case the compound [Ib] can be easily prepared by subjecting said compound [Ib'] to conventional hydrolysis reaction, which is also included within the scope of the present process.

Process 3

The object compound [Id] or its salt can be prepared by subjecting a compound [Ic] or its salt to elimination of the acyl group at the acyloxy group.

This elimination reaction can be carried out in a similar manner to that of conventional hydrolysis.

The hydrolysis can be effected in the presence of an acid such as hydrochloric acid, sulfuric acid, acetic acid, trifluoroacetic acid or p-toluenesulfonic acid or a base such as sodium hydroxide or sodium ethoxide, in alcohol [e.g. methanol, ethanol, etc.], benzene, water or any other solvent which does not adversely affect this reaction.

The reaction temperature is not critical, and the reaction can be carried out under cooling, at ambient temperature or under heating.

The compounds obtained by the above Processes 1 to 3 can be isolated and purified by a conventional method such as pulverization, recrystallization, column chromatography, reprecipitation or the like.

It is to be noted that each of the object compound [I] and the starting compounds may include one or more stereoisomer due to asymmetric carbon atom(s) and all such isomers and mixture thereof are included within the scope of this invention.

The new thiazole compound [I] and pharmaceutically acceptable salts thereof possess antiallergic activity and/or 5-lipoxygenase inhibitory activity and are useful for a therapeutic treatment or prophylaxis of allergic disease such as allergic asthma, allergic rhinitis, allergic conjunctivitis or chronic urticaria.

The compound [I] and a pharmaceutically acceptable salt thereof of this invention can be used in the form of conventional solid, semisolid or liquid pharmaceutical preparations in admixture with conventional organic or inorganic carriers or excipients suitable for oral, parenteral or external application. The active ingredients may be admixed with conventional, nontoxic, pharmaceutically acceptable carriers having the form of, for example, tablets, pellets, capsules, patches, suppositories, solutions, emulsions or suspensions or any other form suitable for use. Usable carriers are not limited to any particular species. Thus, conventional carriers such as water, glucose, lactose, gum arabic, gelatin, mannitol, starch paste, magnesium trisilicate, talc, corn starch, keratin, colloidal silica, potato starch and urea and other carriers suitable for the manufacture of solid, semisolid or liquid preparations can be used. Furthermore, auxiliaries, stabilizers, thickening agents and colorants as well as aromas may be added.

The dose or therapeutically effective amount of the object compound [I] of this invention may vary depending on the age and symptoms of each individual patient to be treated. Generally, the active ingredients are administered for disease treatment in a daily dose of about 0.1–100 mg/kg, preferably 0.1–10 mg/kg.

In order to illustrate the usefulness of the object compound [I], the pharmacological test data of some representative compounds of the compound [I] are shown in the following.

Test Compounds

Compound A: 2-Mesylamino-4-[4-(diphenylmethoxy)-piperidinomethyl]thiazole

Compound B: 2-Propionylamino-4-[4-(diphenylmethoxy)piperidinomethyl]thiazole

Compound C: 2-Butyrylamino-4-[4-(diphenylmethoxy)-piperidinomethyl]thiazole

Compound D: 2-Cyclopropylcarbonylamino-4-[4-(diphenylmethoxy)piperidinomethyl]thiazole Compound E: 2-(D-Lactoylamino)-4-[4-(diphenylmethoxy)piperidinomethyl]thiazole Compound F: 2-Ethoxycarbonylamino-4-[4-(diphenylmethoxy)piperidinomethyl]thiazole Compound G: 2-(3-Methylureido)-4-[4-(diphenylmethoxy)piperidinomethyl]thiazole Test 1

Antagonistic action on anaphylactic asthma in guinea pigs

Male Hartley-strain guinea pigs weighing 305–400 g were used. These animals were sensitized by intravenous injection of 0.5 ml/animal of rabbit antiserum to egg-white albumin (PCA antibody titer 4,000). After 24 hours, the animals were housed individually in 5.3-liter plastic chambers. Using a commercial sprayer, a 5% egg-white albumin solution was sprayed in the form of an aerosol into each chamber at a rate of 0.16 ml/min for 2 minutes. Thirty minutes prior to the spraying of the egg-white albumin solution, the test compound was administered orally in varied concentrations. Each dosed group consisted of 5 animals. The prophylactic effect to anaphylaxis was expressed in terms of the $ED_{50}$ value determined on the basis of the number of guinea pigs which had survived for not less than 2 hours after antigen spraying for each administration concentration of the test compound.

The values thus obtained are given in the following table.

| | Test Results |
|---|---|
| Test Compound | Prophylactic Effect $ED_{50}$ (mg/kg) |
| A | 0.03 |

Test 2

Anti-SRS-A activity (5-lipoxygenase inhibitory activity)

Peritoneal exudate cells were collected from glycogen-injected SD rats and adjusted to $1 \times 10^7$ cells/ml with Tyrode's solution. One milliliter of the cell suspension was incubated with indomethacin (10 μg/ml) and each varied concentration of the test compound for 10 minutes and, then, further incubated with $Ca^{++}$-ionophore (A23187, 1 μg/ml) for 10 minutes. The supernatant was collected by centrifugation and the SRS-A (slow-reacting substance of anaphylaxis) activity was determined in terms of contractility of the isolated guinea pig ileum in the presence of mepyramine, atropine and methysergide.

The results were expressed in terms of the 50% inhibitory concentration to SRS-A synthesis or release from peritoneal exudate cells.

| | Test results |
|---|---|
| Test Compound | Inhibitory Concentration $IC_{50}$ (μg/ml) |
| B | 0.023 |
| C | 0.023 |
| D | 0.011 |
| E | 0.015 |
| F | 0.014 |
| G | 0.015 |

The following Examples are given for the purpose of illustrating the present invention in more detail.

EXAMPLE 1

A stirred mixture of 2-amino-4-chloromethylthiazole hydrochloride (0.7 g), 4-(diphenylmethoxy)piperidine (0.78 g) and triethylamine (1.82 ml) in N,N-dimethylformamide (7.8 ml) was heated at 40° C. to 45° C. for 5 hours. After cooling to ambient temperature, the reaction mixture was filtered. The filtrate was poured into water (50 ml) and extracted with ethyl acetate (80 ml×2). The extract was washed with a saturated aqueous solution of sodium chloride (30 ml) and dried over magnesium sulfate. The solvent was distilled off and the residue was subjected to column chromatography on silica gel (30 g) and eluted with a mixture of chloroform and methanol (10:1 V/V). The fractions containing the object compound were combined and concentrated under reduced pressure to give 2-amino-4-[4-(diphenylmethoxy)piperidinomethyl]thiazole (0.78 g).

IR (Nujol): 3250, 1650, 1535, 1450, 1068 $cm^{-1}$.

NMR (DMSO-$d_6$, δ): 1.6–3.7 (9H, m), 3.40 (2H, s), 5.12 (2H, br s), 5.51 (1H, s), 6.31 (1H, s), 7.1–7.5 (10H, m).

EXAMPLE 2

A stirred mixture of 4-chloromethyl-2-propionylaminothiazole (0.64 g), 4-(diphenylmethoxy)piperidine (0.8 g) and sodium bicarbonate (0.3 g) in N,N-dimethylformamide (8 ml) was heated at 80° to 90° C. for 2 hours. The reaction mixture was poured into ice water. The resulting precipitate was collected, washed with water and dried in vacuo. The precipitate was subjected to column chromatography on silica gel and eluted with a mixture of chloroform and methanol (10:1 V/V). The fractions containing the object compound were combined and concentrated under reduced pressure. The residue was triturated with diisopropyl ether to give white crystals. The crystals were recrystallized from a mixture of toluene and diisopropyl ether and dried under reduced pressure to give 2-propionylamino-4-[4-(diphenylmethoxy)piperidinomethyl]thiazole (0.35 g).

mp: 86°–88° C.

IR (Nujol): 3200, 1685, 1575, 1492 $cm^{-1}$.

NMR (CDCl$_3$, δ): 1.28 (3H, t, J=7.0 Hz), 1.6–3.0 (11H, m), 2.45 (2H, q, J=7.0 Hz), 3.50 (3H, m), 5.50 (1H, s), 6.72 (1H, s), 7.2–7.5 (10H, m).

MASS (m/e): 435 (M+), 167.

Analysis calcd. for $C_{25}H_{29}N_3O_2S \cdot H_2O$ C 66.20, H 6.89, N 9.26. Found: C 66.33, H 6.88, N 9.15.

EXAMPLE 3

The following compounds were obtained according to a similar manner to that of Example 2.

(1) 2-Butyrylamino-4-[4-(diphenylmethoxy)piperidinomethyl]thiazole

IR (Nujol): 3180, 1680, 740, 700 $cm^{-1}$.

(2) 2-Cyclopropylcarbonylamino-4-[4-(diphenylmethoxy)piperidinomethyl]thiazole

IR (Nujol): 3180, 1680, 1545, 1280, 700 $cm^{-1}$.

(3) 2-Isobutyrylamino-4-[4-(diphenylmethoxy)piperidinomethyl]thiazole

IR (Nujol): 3440, 1693, 1550, 1260, 700 $cm^{-1}$.

(4) 2-(2-Acetoxy-2-methylpropionylamino)-4-[4-(diphenylmethoxy)piperidinomethyl]thiazole MASS (m/e): 507 (M+), 167.

(5) 2-Ethoxycarbonylamino-4-[4-(diphenylmethoxy)piperidinomethyl]thiazole

IR (Nujol): 3450, 1720, 1547, 1230, 700 $cm^{-1}$.

(6) 2-Mesylamino-4-[4-(diphenylmethoxy)piperidinomethyl]thiazole

IR (Nujol): 1440, 1285, 1120 $cm^{-1}$.

(7) 2-(D-Lactoylamino)-4-[4-(diphenylmethoxy)piperidinomethyl]thiazole

MASS (m/e): 451 (M+).

(8) 2-(L-Lactoylamino)-4-[4-(diphenylmethoxy)piperidinomethyl]thiazole

MASS (m/e): 451 (M+).

(9) 2-((2R)-2-Acetoxypropionylamino)-4-[4-(diphenylmethoxy)piperidinomethyl]thiazole

(10) 2-((2S)-2-Acetoxypropionylamino)-4-[4-(diphenylmethoxy)piperidinomethyl]thiazole

(11) 2-(2-Hydroxy-2-methylpropionylamino)-4-[4-(diphenylmethoxy)piperidinomethyl]thiazole MASS (m/e): 465 (M+).

(12) 2-(3-Methylureido)-4-[4-(diphenylmethoxy)piperidinomethyl]thiazole

MASS: 436 (M+), 167.

(13) 2-Ethylsulfonylamino-4-[4-(diphenylmethoxy)piperidinomethyl]thiazole

MASS (m/e): 471 (M+).

EXAMPLE 4

To a stirred mixture of 2-amino-4-[4-(diphenylmethoxy)piperidinomethyl]thiazole (8.04 g) and pyridine (7.72 ml) in dry N,N-dimethylformamide (80 ml) was added slowly a solution of propionyl chloride (2.76 ml) in dichloromethane (2 ml) at a temperature below 5° C. After 30 minutes, the reaction mixture was poured into ice water (800 ml) and extracted with ethyl acetate (400 ml), and the extract was dried over magnesium sulfate. The solvent was distilled off and purified by column chromatography on silica gel to give 2-propionylamino- 4-[4-(diphenylmethoxy)piperidinomethyl]thiazole (8.9 g).

This compound was identified with the compound obtained in Example 2 by physical data thereof.

EXAMPLE 5

The following compounds were obtained according to a similar manner to that of Example 4.

(1) 2-Butyrylamino-4-[4-(diphenylmethoxy)-piperidinomethyl]thiazole mp: 84°–88° C. (recrystallized from 60% ethanol).

IR (Nujol): 3180, 1680, 740, 700 cm$^{-1}$.

NMR (DMSO-d$_6$, δ): 0.9 (3H, t, J=6.6 Hz), 1.2–3.6 (13H, m), 3.47 (2H, s), 5.64 (1H, s), 6.90 (1H, s), 7.2–7.6 (10H, m), 11.87 (1H, s).

MASS (m/e): 450 (M+), 167.

Analysis calcd. for C$_{26}$H$_{31}$N$_3$O$_2$S.H$_2$O C 66.78, H 7.11, N 8.99. Found: C 66.50, H 7.03, N 8.95.

(2) 2-Cyclopropylcarbonylamino-4-[4-(diphenylmethoxy)piperidinomethyl]thiazole mp: 82°–88° C. (recrystallized from 60% ethanol).

IR (Nujol): 3180, 1680, 1545, 1280, 700 cm$^{-1}$.

NMR (DMSO-d$_6$, δ): 0.8–1.0 (4H, m), 1.5–3.9 (10H, m), 3.66 (2H, s), 5.64 (1H, s), 7.02 (1H, s), 7.2–7.6 (10H, m), 12.2 (1H, s).

Analysis Calcd. for C$_{26}$H$_{29}$N$_3$O$_2$S.4/5H$_2$O C 67.59, H 6.73, N 9.10. Found: C 67.62, H 6.53, N 9.00.

(3) 2-Isobutyrylamino-4-[4-(diphenylmethoxy)-piperidinomethyl]thiazole mp: 81°–93° C. (recrystallized from 80% ethanol).

IR (Nujol): 3440, 1693, 1550, 1260, 700 cm$^{-1}$.

NMR (DMSO-d$_6$, δ): 1.10 (6H, t, J=6.8 Hz), 1.2–3.7 (10H, m), 3.46 (2H,s), 5.64 (1H, s), 6.90 (1H, s), 7.1–7.6 (10H, m).

MASS (m/e): 449 (M+), 167.

Analysis Calcd. for C$_{26}$H$_{31}$N$_3$O$_2$S.H$_2$O C 66.78, H 7.11, N 8.99. Found: C 66.70, H 7.09, N 8.90.

(4) 2-(2-Acetoxy-2-methylpropionylamino)-4-[4(diphenylmethoxy)piperidinomethyl]thiazole NMR (DMSO-d$_6$, δ): 1.53 (6H, s), 2.03 (3H, s), 1.4–3.6 (9H, m), 3.43 (2H, s), 5.62 (1H, s), 5 6.93 (1H, s), 7.1–7.6 (10H, m), 11.9 (1H, s).

MASS (m/e): 507 (M+) 167.

(5) 2-Ethoxycarbonylamino-4-[4-(diphenylmethoxy)-piperidinomethyl]thiazole

IR (Nujol): 3450, 1720, 1547, 1230, 700 cm$^{-1}$.

NMR (CDCl$_3$, δ): 1.31 (3H, t, J=7.4 Hz), 1.5–3.7 (9H, m), 3.53 (2H, s), 4.30 (2H, q, J=7.4 Hz), 5.51 (1H, s), 6.72 (1H, s), 7.1–7.6 (10H, m).

MASS (m/e): 451 (M+), 167.

(6) 2-((2R)-2-Acetoxypropionylamino)-4-[4-(diphenylmethoxy)piperidinomethyl]thiazole NMR (CDCl$_3$, δ): 1.55 (3H, d, J=7.5 Hz), 1.5–3.6 (9H, m), 2.17 (3H, s), 3.53 (2H, s), 5.40 (1H, q, J=7.5 Hz), 5.47 (1H, s), 6.77 (1H, s), 7.1–7.4 (10H, m).

(7) 2-((2S)-2-Acetoxypropionylamino)-4-[4-(diphenylmethoxy)piperidinomethyl]thiazole NMR (CDCl$_3$, δ): 1.55 (3H, d, J=7.5 Hz), 1.5–3.6 (9H, m), 2.17 (3H, s), 3.53 (2H, s), 5.40 (1H, q, J=7.5 Hz), 5.47 (1H, s), 6.77 (1H, s), 7.1–7.4 (10H, m).

(8) 2-(D-Lactoylamino)-4-[4-(diphenylmethoxy)-piperidinomethyl]thiazole

MASS (m/e): 451 (M+).

(9) 2-(L-Lactoylamino)-4-[4-(diphenylmethoxy)-piperidinomethyl]thiazole

MASS (m/e): 451 (M+).

(10) 2-(2-Hydroxy-2-methylpropionylamino)-4-[4-(diphenylmethoxy)piperidinomethyl]thiazole MASS (m/e): 465 (M+).

EXAMPLE 6

To a stirred mixture of 2-amino-4-[4-(diphenylmethoxy)piperidinomethyl]thiazole (0.78 g), N-methylmorpholine (1.15 ml) in N,N-dimethylformamide (8 ml) was added dropwise a solution of methanesulfonyl chloride (0.5 g) in dichloromethane (0.5 ml) under ice-bath cooling. After 1 hour, the reaction mixture was filtered. The filtrate was made basic with 1N sodium hydroxide solution (12 ml). After being stirred for 30 minutes, the mixture was neutralized with 1N hydrochloric acid and extracted with dichloromethane (40 ml×2). The extract was washed with a saturated aqueous solution of sodium chloride and dried over magnesium sulfate. The solvent was distilled off and the residue was subjected to column chromatography on silica gel, and eluted with a mixture of chloroform and methanol (10:1 V/V). The fractions containing the object compound were combined and concentrated under reduced pressure to give white crystals. The crystals were recrystallized from ethanol to give 2-mesylamino-4-[4-(diphenylmethoxy)piperidinomethyl]thiazole (0.32 g).

IR (Nujol): 1440, 1285, 1120 cm$^{-1}$.

NMR (DMSO-d$_6$, δ): 1.5–2.9 (8H, m), 2.96 (3H, s), 3.38 (3H, br s), 5.62 (1H, s), 6.55 (1H, s), 6.9–7.4 (11H, m).

MASS (m/e): 457 (M+) 167.

Analysis calcd. for C$_{23}$H$_{27}$N$_3$O$_3$S$_2$ C 60.37, H 5.95, N 9.18. Found: C 60.24, H 5.94, N 9.11.

EXAMPLE 7

2-Ethylsulfonylamino-4-[4-(diphenylmethoxy)-piperidinomethyl]thiazole was obtained according to a similar manner to that of Example 6.

mp: 190°–191° C.

IR (Nujol): 1294, 1114, 907, 700 cm$^{-1}$.

NMR (DMSO-d$_6$, δ): 1.22 (3H, t, J=7.8 Hz), 1.3–2.8 (8H, m), 2.95 (2H, q, J=7.8 Hz), 3.32 (2H , s), 3.40 (1H, m), 5.60 (1H, s), 6.50 (1H, s), 7.0–7.5 (10H, m).

MASS (m/e): 471 (M+).

Analysis calcd. for C$_{24}$H$_{29}$N$_3$O$_3$S$_2$ C 61.12, H 6.20, N 8.91. Found: C 61.24, H 6.02, N 8.88.

EXAMPLE 8

To a stirred solution of 2-amino-4-[4-(diphenylmethoxy)piperidinomethyl]thiazole (1.0 g) in dry tetrahydrofuran (10 ml) was added dropwise methyl isocyanate (0.34 ml) at ambient temperature. After the addition had been completed, the reaction mixture was stirred for 3 hours. 1N Sodium hydroxide solution (3 ml) was added thereto and stirring was continued for 30 minutes. The reaction mixture was concentrated under reduced pressure and the residue was extracted with ethyl acetate. The extract was washed with a saturated aqueous solution of sodium chloride and dried over magnesium sulfate. After removal of solvent, the residue was subjected to column chromatography on silica gel and eluted with a mixture of chloroform and methanol (20:1 V/V). The fractions containing the object compound were combined and concentrated under reduced pressure. The residue was triturated with 70% ethanol to give white powder. Recrystallization from 70% ethanol gave 2-(3-methylureido)-4-[4-(diphenylmethoxy)-piperidinomethyl]thiazole (0.3 g).

mp: 181°–184° C.

IR (Nujol): 3300 (br), 1720, 1068, 740 cm$^{-1}$.

NMR (CDCl₃, δ): 1.5–3.6 (9H, m), 2.86 (3H, d, J=6.0 Hz), 3.46 (3H, s), 5.49 (1H, s), 6.54 (1H, s), 7.0–7.5 (10H, m), 10.9 (1H, br s).

MASS: 436 (M+), 167.

Analysis calcd. for $C_{24}H_{28}N_4O_2S$ C 66.03, H 6.46, N 12.83. Found: C 65.64, H 6.23, N 12.67.

EXAMPLE 9

A mixture of 2-(2-acetoxy-2-methylpropionylamino)-4-[4-(diphenylmethoxy)piperidinomethyl]thiazole (1.1 g), 1N sodium hydroxide (2.2 ml) and ethanol (23 ml) was heated at 40° C. with stirring for 6 hours. The reaction mixture was concentrated under reduced pressure and the residue was extracted with a mixture of chloroform and methanol (10:1 V/V). The extract was washed with a saturated aqueous solution of sodium chloride and dried over magnesium sulfate. The solvent was distilled off and the residue was pulverized with 70% ethanol and collected by filtration. Recrystallization from 70% ethanol gave 2-(2-hydroxy-2-methylpropionylamino)-4-[4-(diphenylmethoxy)piperidinomethyl]thiazole (0.65 g).

mp: 180°–181° C.

IR (Nujol): 3310, 1705, 1180, 738, 697 cm⁻¹.

NMR (DMSO-d₆, δ): 1.35 (6H, s), 1.4–3.4 (9H, m), 3.41 (2H, s), 5.58 (1H, s), 6.91 (1H, s), 7.1–7.5 (10H, m).

MASS (m/e): 465 (M+).

Analysis calcd. for $C_{26}H_{31}N_3O_3S$ C 67.07, H 6.71, N 9.02. Found: C 67.02, H 6.54, N 8.92.

EXAMPLE 10

To an ice-cooled mixture of 2-((2R)-2-acetoxypropionylamino)-4-[4-(diphenylmethoxy)piperidinomethyl]thiazole (2.1 g), water (4 ml) and methanol (17 ml) was added dropwise 1N sodium hydroxide solution (3 ml). After the addition had been completed, the reaction mixture was kept at 5° C. for 1 hour and allowed to warm to ambient temperature. After standing overnight at the same temperature, the reaction mixture was concentrated under reduced pressure. The residue was extracted with ethyl acetate. The extract was washed with a saturated aqueous solution of sodium chloride and dried over magnesium sulfate. The solvent was distilled off and the residue was subjected to column chromatography on silica gel and eluted with a mixture of chloroform and methanol (30:1 V/V). The fractions containing the object compound were combined and concentrated under reduced pressure. The residue was triturated with 70% ethanol to give white powder. Recrystallization from 70% ethanol gave 2-(D-lactoylamino)-4-[4-(diphenylmethoxy)piperidinomethyl]thiazole (1.13 g).

mp: 75°–83° C.

$[\alpha]_D^{22} = -59.8°$ (c=1.0, CHCl₃).

IR (Nujol): 3300, 1680, 1330, 1168, 697 cm⁻¹.

NMR (CDCl₃, δ): 1.45 (3H, d, J=7.2 Hz), 1.5–3.9 (13H, m), 4.40 (1H, q, J=7.2 Hz), 5.43 (1H, s), 6.60 (1H, s), 7.0–7.5 (10H, m), 12.10 (1H, br s).

MASS: 451 (M+).

Analysis calcd. for $C_{25}H_{29}N_3O_3S.1/3C_2H_5OH$ C 65.28, H 6.56, N 8.91. Found: C 66.02, H 6.69, N 9.00.

EXAMPLE 11

2-(L-Lactoylamino)-4-[4-(diphenylmethoxy)-piperidinomethyl]thiazole was obtained according to a similar manner to that of Example 10.

mp: 82°–87° C.

$[\alpha]_D^{22}$: 63.3° (c=1.0, CHCl₃).

MASS (m/e): 451 (M+).

Analysis calcd. for $C_{25}H_{29}N_3O_3S.2/5C_2H_5OH$ C 64.66, H 6.79, N 8.88. Found: C 64.91, H 6.73, N 8.94.

What we claim is:

1. A thiazole compound of the formula:

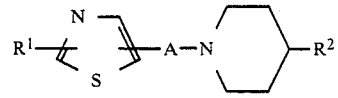

wherein
R¹ is amino, lower alkanoylamino, lower alkanoylamino, mono- or di- or tri-halo(lower)alkanoylamino, cyclo(lower)alkylcarbonylamino, lower alkoxycarbonylamino, hydroxy(lower)alkanoylamino, lower alkanoyloxy(lower)alkanoylamino, lower alkylureido, ureido, benzoylamino, toluoylamino, xyloylamino, naphthoylamino, furoylamino, thenoylamino, nicotinoylamino, isonicotinoylamino, phenylacetylamino, tolylacetylamino, naphthylacetylamino, 2-phenylpropionylamino, 3-phenylpropionylamino, 4-phenylbutyrylamino, tritylcarbonylamino, lower alkylsulfonylamino, tosylamino or phenylsulfonylamino, R² is benzyloxy, phenethyloxy, diphenylethoxy, diphenylpropoxy, trityloxy or diphenylmethoxy, and A is lower alkylene, or a pharmaceutically acceptable salt thereof.

2. A compound of claim 1, wherein
R¹ is lower alkanoylamino, cyclo(lower)alkylcarbonylamino, lower alkoxycarbonylamino, hydroxy(lower)alkanoylamino, lower alkanoyloxy(lower)alkanoylamino, lower alkylureido or lower alkylsulfonylamino, and R² is diphenylmethoxy.

3. A compound of claim 2, wherein R¹ is lower alkanoylamino or lower alkylsulfonylamino.

4. A compound of claim 3, which is 2-mesylamino-4-[4-(diphenylmethoxy)piperidinomethyl]thiazole.

5. A compound of claim 3, which is 2-propionylamino-4-[4-(diphenylmethoxy)piperidinomethyl]thiazole.

6. An antiallergenic pharmaceutical composition comprising an effective amount of a compound of claim 1, as an active ingredient, in association with a pharmaceutically acceptable, substantially nontoxic carrier or excipient.

7. A method for the therapeutic treatment of allergic disease which comprises administering an effective amount of a compound of claim 1 in human beings or animals.

8. The pharmaceutical composition of claim 6, wherein said compound is 2-mesylamino-4-[4-(diphenylmethoxy)piperidinomethyl]thiazole.

9. The pharmaceutical composition of claim 6, wherein said compound is 2-propionylamino-4-[4-(diphenylmethoxy)piperidinomethyl]thiazole.

10. The method of claim 7, wherein said compound is 2-mesylamino-4-[4-(diphenylmethoxy)piperidinomethyl]thiazole.

11. The method of claim 7, wherein said compound is 2-propionylamino-4-[4-(diphenylmethoxy)-piperidinomethyl]thiazole.

* * * * *